United States Patent [19]

Sunano et al.

[11] Patent Number: 4,507,643
[45] Date of Patent: Mar. 26, 1985

[54] GAS SENSOR WITH IMPROVED PEROVSKITE TYPE MATERIAL

[76] Inventors: Naomasa Sunano, 2-12-14, Sawano-nishi, Akashi-shi, Hyogo-ken; Naotatsu Asahi, 3-16-19, Higashiohshima, Katsuta-shi, Ibaraki-ken; Toshio Yoshida, 173-14, Kamihiruta, Kasukabe-shi, Saitama-ken, all of Japan

[21] Appl. No.: 518,110

[22] Filed: Jul. 28, 1983

[30] Foreign Application Priority Data

Aug. 6, 1982 [JP] Japan .................. 57-136244

[51] Int. Cl.$^3$ .......................... G01N 27/12
[52] U.S. Cl. ........................... 338/34; 73/23; 422/94; 422/98
[58] Field of Search ............ 338/34; 73/23, 27 R; 422/94, 98; 204/425, 426

[56] References Cited

U.S. PATENT DOCUMENTS

| | | | |
|---|---|---|---|
| 3,695,848 | 4/1970 | Taguchi | 73/27 R X |
| 3,699,803 | 10/1972 | Sumi et al. | 338/34 X |
| 3,951,603 | 4/1976 | Obayashi et al. | 338/34 X |
| 3,953,173 | 4/1976 | Obayashi et al. | 338/34 X |
| 4,044,601 | 8/1976 | Sakurami et al. | 338/34 X |
| 4,221,827 | 9/1980 | Parray et al. | 73/23 X |
| 4,296,148 | 10/1981 | Friese | 204/426 X |
| 4,304,652 | 12/1981 | Chiba et al. | 204/426 |
| 4,314,996 | 2/1982 | Sekido et al. | 338/34 X |
| 4,322,968 | 4/1982 | Takami et al. | 338/34 X |
| 4,338,281 | 7/1982 | Treitinger et al. | 422/98 |
| 4,351,182 | 9/1982 | Schmidberger | 338/34 X |
| 4,443,781 | 4/1984 | Ohata et al. | 338/34 |

FOREIGN PATENT DOCUMENTS

55104 6/1982 European Pat. Off. .............. 338/34

Primary Examiner—Roy N. Envall, Jr.
Assistant Examiner—C. N. Sears
Attorney, Agent, or Firm—Antonelli, Terry & Wands

[57] ABSTRACT

A gas sensor is described which includes a layer of a sensitive material formed on an electric insulating substrate and spaced electrodes electrically connected to the layer. The layer is formed of a porous film of a uniform mixture which contains a p-type compound oxide semiconductor with a perovskite type of crystal structure as the major ingredient and one or more of vanadium, niobium, tantalum and/or compounds thereof as minor ingredients. The minor ingredients are contained in the layer in an amount of 0.01 to 5% by weight, based on the weight of the p-type compound oxide semiconductor, and are incorporated into the layer by diffusing them into the layer. The gas sensor exhibits a small change with time and a reduced tailing effect attendant on variations in the gas combustion. With this, it is possible to effect measurements, detection and control with a high reliability.

16 Claims, 13 Drawing Figures

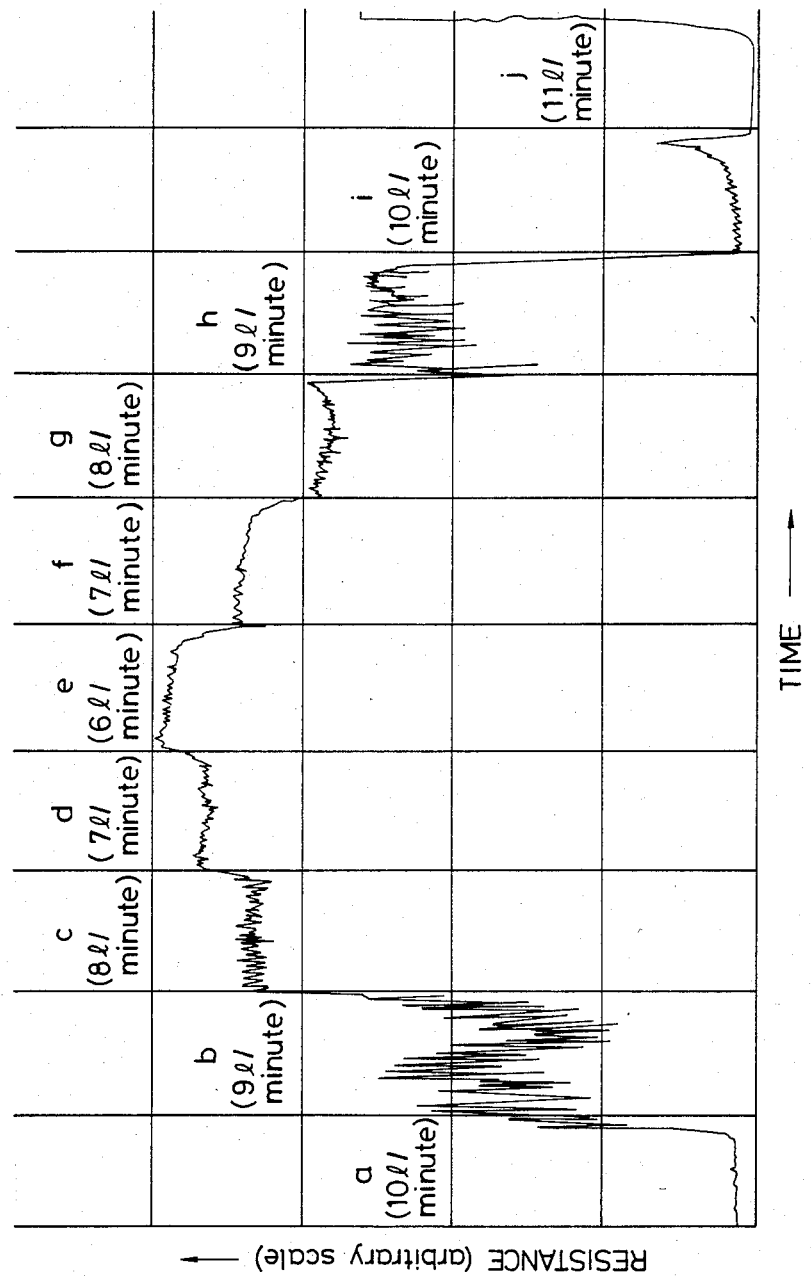

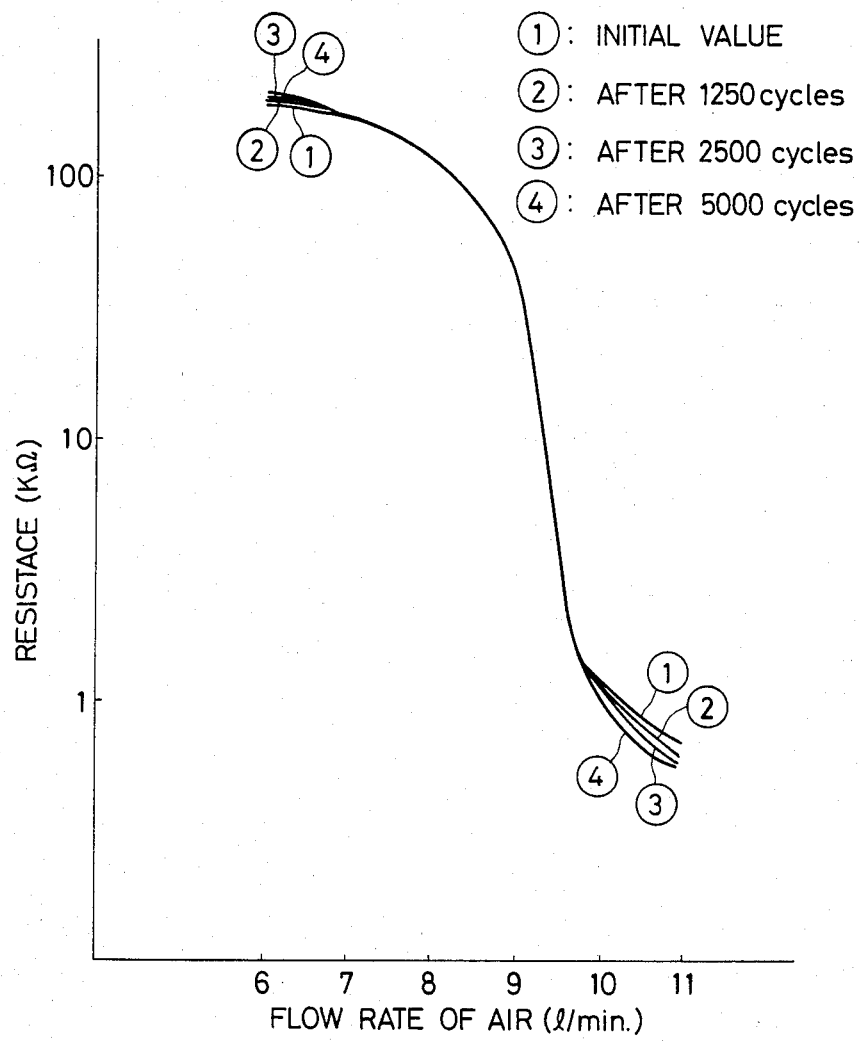

GAS SENSOR WITH IMPROVED PEROVSKITE TYPE MATERIAL

FIELD OF THE INVENTION

This invention relates to a gas sensor and a method of manufacturing the same which uses perovskite types of compound oxides represented by $ABO_3$ (where A is a rare-earth element, part of which may be replaced by an alkaline earth metal, and B is one or more transition metal elements) as a sensitive material, and more particularly to a gas sensor and a method of manufacturing the same which has a reduced level of changes in the characteristics of the sensitive material due to the adsorption and release of gases.

The gas sensor of this invention can be used to measure the contents of gas components such as oxygen, hydrocarbons, alcohol, moisture, carbon monoxide, etc., contained in combustion exhaust gases, flames, air and other gaseous bodies, as well as control the contents of gas components based on such a measurement.

BACKGROUND OF THE INVENTION

A compound oxide represented by $ABO_3$ (where A is a rare-earth element, part of which may be replaced by an alkaline earth metal, and B is one or more transition metal elements) offers a p-type semiconductor with perovskite types of crystal structure. It has been proposed that a semiconductor of this type is used as a sensitive material for a gas sensor, because the value of its resistance is reduced with, for example, an increase of the oxygen content in a gas.

U.S. Pat. No. 3,951,603 (Gas-sensor Element and Method for Detecting Reducing Gas or Oxygen Gas) discloses a gas sensor in which a paste including a perovskite type of compound oxide semi-conductor is coated and sintered onto an alumina substrate, and which is sensitive to a reducing gas.

U.S. Pat. No. 3,953,175 (Gas-sensor Element and Method for Detecting Oxidizable Gas) discloses a gas sensor which employs a sensitive material consisting of a mixture of perovskite types of compound oxides and $K_2Mg_4$.

U.S. Pat. No. 4,044,601 (Smoke and Gas Sensor Element) discloses a gas sensor which employs a sensitive material consisting of a mixture of perovskite types of compound oxides and CdO, $In_2O_3$, SnO, $Tl_2O_3$ or PbO.

Further, a gas sensor using perovskite types of compound oxides as a sensitive material is also disclosed in U.S. Pat. No. 4,221,827, Japanese Patent Laid Open No. 132941/1980, No. 144391/1975, No. 8537/1981, No. 110385/1975, No. 166030/1980, No. 31631/1981, No. 35533/1981 and No. 166459/1981.

With such a gas sensor using perovskite types of compound oxide semiconductors as a sensitive material, it has been observed that some change occurs with the lapse of time, if the composition of, for example, a combustion exhaust gas, particularly the oxygen content, varies. More specifically, if a sensor is first exposed to perfect combustion flames and then to imperfect combustion flames, the value of the electric resistance of the sensitive material changes with time. When the sensor is returned into the perfect combustion flames once again, the value of its resistance is not restored to its original value instantaneously, but it returns gradually to it original value in equilibrium with the gas content over a certain period of time.

As shown in FIG. 1, as a result of combustion experiments using a gas sensor which employs a sensitive material consisting of only a p-type perovskite compound oxide ($LaNiO_3$), it has been found that the value of the resistance of the sensor increases, when the conditions it is exposed to shift from a perfect combustion region a (where the flow rate of air is 10 l/min to 0.1 l of propane) to a region b where the flow rate of air is reduced to 9 l/min, in the presence of secondary air. When the flow rate of air is further reduced to 8 l/min, the resistance increases more (region c). After a reduction in the flow rate of air to 7 l/min (region d) and then 6 l/min (region e), even when the flow rate is increased gradually once again to 7 l/min (region f), 8 l/min (region g) and then 9 l/min (region h), the resistance does not return back to its original value and takes a somewhat higher value. The time period of each region in FIG. 1 corresponds to 1 minute.

It is desired that an ideal gas sensor offers the same value of resistance at all times under identical combustion conditions.

The above change with time in the perovskite types of compound oxide semiconductors probably results from a reversible change or conversion of the conductivity type of the compound oxide itself attendant on the adsorption and release of oxygen molecules as well as reducing substances (such as carbon monoxide), or from the influence of changes in temperature. In particular, chemical changes due to the adsorption and release of gas molecules are likely to appear with a time lag in the diffusion process of the gas molecules between the surface and the interior of the p-type perovskite compound oxide. This phenomenon (referred to as a tailing effect in this invention) can be also observed in n-type oxide semiconductors (such as tin oxide).

However, such a tailing effect is very disadvantageous in gas sensors used in fields where combustion conditions vary frequently, including combustion control based on the oxygen content or carbon monoxide content in the exhaust gas from motor vehicles as well as combustion controls of domestic heating appliances and boilers.

BRIEF DESCRIPTION OF THE DRAWINGS

FIG. 1 is a graph showing the relationship between changes in resistance and air/fuel ratio of a prior art gas sensor using a p-type perovskite;

FIGS. 6(a), 6(b) and 6(c) are graphs showing the results of resistance to flame tests, heat resistance cycle tests and heat resistance tests made on gas sensors of this invention, respectively;

SUMMARY OF THE INVENTION

Figure 2A:
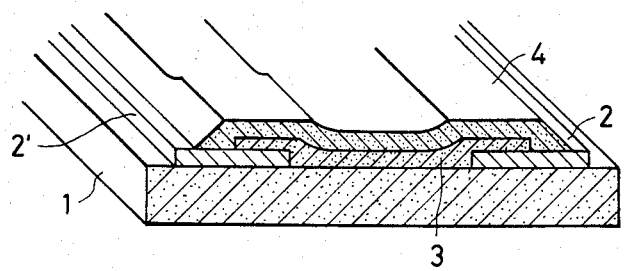
FIG. 2(a) is a sectioned perspective view showing the structure of an essential part of the gas sensor according to one embodiment of this invention.

It is an object of this invention to provide a gas sensor and a method of manufacturing the same which has sensitive characteristics which respond promptly to fluctuations of combustion conditions, particularly the air/fuel ratio, or changes in the contents of detected materials contained in the gas being measured.

This invention is related to a gas sensor in which the degree of changes with time, i.e., the tailing effect, is reduced by utilizing the fact that p-type compound oxide semiconductors with a perovskite type of structure have superior gas sensitive characteristics. More specifically, this invention is related to a gas sensor featured in using a sensitive material which is formed by adding a small amount of a given element or a compound thereof to a p-type compound oxide semiconductor.

This invention is also related to a method of manufacturing a gas sensor using a p-type perovskite compound oxide semiconductor which has the most sensitive characteristics and which exhibits a tailing effect which is reduced or completely eliminated.

DESCRIPTION OF THE INVENTION

(a) P-type perovskite compound oxides

As disclosed in the above publications, gas sensors using perovskite compound oxides are well known. Although such compound oxides can be used in this invention, it is desirable to use p-type compound oxide semiconductors. A p-type semiconductor has the property that the value of the resistance thereof increases with a reduction in oxygen content. Therefore, even if a sensitive film of the gas sensor is broken and hence its resistance is increased to infinity, this state will issue a signal preventing imperfect combustion. On the other hand, when a n-type semiconductor is used, its resistance decreases in imperfect combustion regions, thereby generating the fear that combustion appliances may run recklessly if the gas sensor malfunctions. An additional protective circuit is necessary to eliminate such a fear and this leads to a complicated structure and the increased cost of the gas sensor.

Perovskites are represented by the general expression $ABO_3$. In this expression, A is a lanthanoid such as lanthanum, cerium or praseodymium, part of which may be replaced by an alkaline earth metal, for example strontium. B is transition metal elements such as nickel, chromium, titanium, copper, cobalt or vanadium.

More concretely, $ABO_3$ is given by the following: $LaNiO_3$, $LaCrO_3$, $LaTiO_3$, $LaCuO_3$, $PrTiO_3$, $CeTiO_3$, $La_{1-x}Sr_xVO_3$ $(0.1 \leq x \leq 0.4)$, $La_{1-x}Sr_xTiO_3$ $(0.1 \leq x \leq 0.4)$, etc.

(b) Method of forming perovskite compound oxide film

According to this invention, the desired electrode films are first formed on an electrically insulative substrate such as alumina, and then a compound oxide film is formed by an appropriate process so that a sensitive material layer thereof is electrically connected to those electrodes. As an alternative, the electrode films may be sintered onto the substrate after the formation of the sensitive material layer.

A study of perovskite compound oxide films made by the inventors has proved that the state of the films is very important in obtaining the desired sensitive characteristics. According to the above well-known publications, perovskite compound oxide films are formed in such a manner that a powder of perovskite compound oxides is dispersed into methyl cellulose or the like to obtain a paste, and this paste is printed and sintered onto an alumina substrate.

However, since perovskites themselves have a low sintering property, the adhesion force of the films onto the alumina substrate is weak, and they tend to separate therefrom easily.

The inventors have studied various methods with which fine powder of perovskite compound oxides can be made to adhere closely to electrically insulative substrates. As a result, the following methods were found to be effective.

(i) Plasma spray coating

A fine powder of perovskite compound oxides (less than 1 μm, preferably in the range of 100 Å to 5000 Å) is spray coated onto an electrically insulative substrate by the well-known process of plasma spray coating. The obtained film is preferred to have the most uniform and thinnest possible thickness, the practical thickness is in the range of 0.5 to 50 μm, preferably 1 to 10 μm.

With this plasma spray coating method, perovskite powder strikes against the surface of the substrate with a strong force, so that part of the sprayed powder fuses into or is mechanically united with the substrate thereby achieving a strong and close adhesion to it. Thus, it is not required basically to use glass binders unlike in the conventional paste printing and sintering methods. It is a matter of course that such binders may be added within a non-detrimental range.

A more effective advantage of the plasma spray coating film is in that a number of fine cracks are formed in the film. More specifically, the diffusion of gas molecules during adsorption and release is essential to the reaction of a gas sensor. Because of the thin spray coating film and the presence of the fine cracks, the diffusion of gas molecules is made rapidly in this invention, whereby the sensitivity of the present gas sensor is increased by so much.

(ii) Chemical vapor deposition (CVD) method

The desired film can be also coated in such a manner that a halide of a lanthanide series and a halide of a transition metal are introduced into a reaction furnace using a carrier gas. For $LaNiO_3$, or example, lanthanum chloride and nickel chloride are introduced into the reaction furnace using a carrier gas consisting of argon plus 5% hydrogen. The amounts of lanthanum chloride and nickel chloride are adjusted to be approximately 1:1 in mol ratio after the decomposition. Oxygen is added to the reaction furnace using argon as the carrier and the pressure is adjusted to be higher than 80 torr. The surface of the insulative substrate preheated to above 600° C. is then exposed to the reaction gas, thereby obtaining a porous $LaNiO_3$ film.

(iii) Physical vapor deposition (PVD) method

An unalloyed or alloyed plate of lanthanum or nickel is disposed within a vacuum furnace as a negative pole, and an alumina substrate is provided opposite to and adjacent to the negative pole. On this occasion, a positive pole is provided within the furnace separately, or the furnace wall serves as a positive pole.

After reducing the pressure within the furnace to about $10^{-6}$ torr, argon gas containing oxygen is introduced thereto and the pressure is adjusted to be between $10^{-3}$ to $10^{-1}$ torr. In this state, a direct current of 0.8 to 5.0 kV is applied across the two poles. A sputtering process is carried out to form a porous $LaNiO_3$ layer approximately 3 μm thick on the substrate preheated up to about 600° C.

(c) Formation of electrodes

A paste of a heat resistant metal powder such as platinum is printed and sintered on the electrically insulative substrate such as alumina to form the desired platinum electrodes. A perovskite compound oxide film is formed over these electrodes. As an alternative, similar electrodes may be formed in a sequence the reverse of the above.

(d) Permeable inorganic insulative film

In order to protect the perovskite compound oxide film or the electrodes from mechanical shocks, a permeable and heat resistant inorganic insulative film is formed over the film. This insulative film must be permeable to gas, so it is preferable to utilize a plasma spray coating method because it is suitable for forming porous films. A similar insulative film can also be obtained by utilizing a PVD method.

A stable and neutral inorganic substance such as alumina is suitable for such an inorganic insulative film.

(e) Addition of Va-series elements or compounds thereof

It has been found that the three elements of vanadium, niobium and tantalum and the compounds thereof are effective in reducing or eliminating the above tailing effect.

Although the action of oxides of these elements is not yet fully understood, it is presumed that the oxides of these elements contribute to the stabilization of p-type perovskite compound oxides when added to the compound oxides, because they have a tendency to form n-type semiconductors. However, if the amount of these additional oxides becomes too large, the sensitive characteristics of the p-type perovskite compound oxides will be reduced. For general uses, such an additional amount is preferably in the range of 0.01 to 5% by weight (percentage of the amount of added oxides to that of the compound oxides), particularly between 0.1 to 2% by weight.

Methods used for adding the oxides are as follows.

(i) Gaseous diffusion method

A substrate having a spray coating film of a p-type perovskite compound oxide is set in a vapor atmosphere of the element or a compound thereof which is to be added, and it is heated to diffuse the given oxide.

(ii) Impregnation method

A solution of the element or a compound thereof to be added is impregnated into the spray coating film, and after drying, the film is heated for diffusion in an oxidizing atmosphere. As an alternative, a permeable insulative film is formed over the perovskite compound oxide film, the above solution is impregnated into the compound oxide film through the insulative film, and then after drying, the compound oxide film is heated for diffusion in an oxidizing atmosphere.

(iii) Power-preparing method

In the stage in which a powder of the sensitive material to be formed onto the alumina substrate is prepared, the desired amount of the element or a compound thereof to be added is previously mixed with the p-type perovskite compound oxide powder, and then it is sintered in an oxidizing atmosphere.

When preparing the solution of the element to be added, it is preferable to use compounds of carbon, hydrogen, oxygen or nitrogen which are easily dissipated after decomposition, and which include no deterimental elements such as chloride or sodium. By way of example, an aqueous solution of $NH_4VO_3$ or an oxalic acid solution of $Nb(HC_2O_4)_5$ can be used. As to halides, chlorides, fluorides or bromides are available. For example, a nitric acid solutin of $NbF_5$ or an aqueous solution of $TaF_5$ is used in practice. These solutions become oxides when sintered in an oxidizing atomosphere.

As will be seen from Japanese Patent Laid Open No. 46452/1981 of the above publications, it is known that some of the Ni or Co contained in $LaNiO_3$ or $LaCoO_3$ is replaced by Mn or other elements. But these compound oxides are basically genuine p-type perovskites. On the other hand, in the sensitive material of this invention, a given element or a compound thereof is diffused or dispersed into a p-type perovskite compound oxide, so that the sensitive material constitutes a mixed system. It should be understood that the tailing effect inherent in p-type perovskites can be reduced or eliminated by the presence of such a mixed system. In other words, this invention is different from the above prior art in that the sensitive material of the former does not consist of genuine or complete perovskites.

(f) Applications of gas sensor

In this invention, in addition to the sensitive material layer and the electrodes formed on a single electrical insulative substrate, a platinum heater and the electrodes thereof, a thermistor and the electrodes thereof, or a layer of another oxide semiconductor, for example an n-type oxide semiconductor layer, and the electrodes thereof may be provided additionally.

When a heater is provided, it an be used to preheat or heat the gas sensor in a gas of a low temperature and maintain the sensor at a predetermined temperature, so that the target sensitive characteristics may be obtained desirously.

When a thermistor is provided, it becomes possible to measure the temperature of the gas. As required, the measured gas temperature can also be utilized to correct the gas sensor or control the gas temperature.

When an n-type oxide semiconductor is provided, the measurement and detection of gas can be performed with a smaller influence of noise due to differences in electromotive forces between the n-type oxide semiconductor film and the p-type perovskite compound oxide semiconductor.

The gas sensor of this invention is applicable to measuring the contents of oxygen, carbon monoxide, alcohol, hydrocarbon, moisture, etc., as well as control the gas contents based on the measured result.

DESCRIPTION OF DRAWINGS AND EMBODIMENTS

Figure 3A:
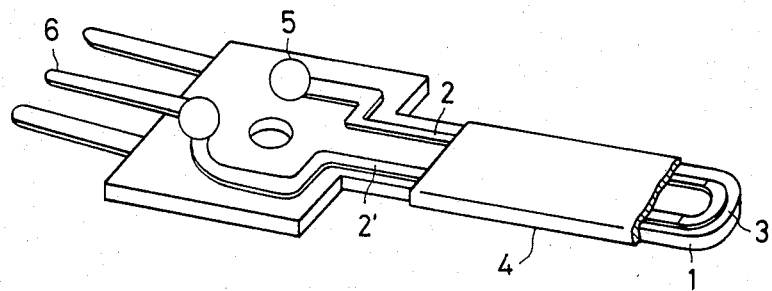
FIG. 3(a) is a plan view of the gas sensor according to another embodiment of this invention.
Figure 3B:
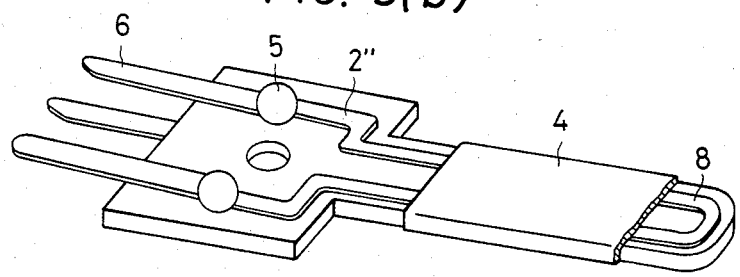
FIG. 3(b) is a plan view of the opposite face of the sensor of FIG. 3(a)
Figure 4:
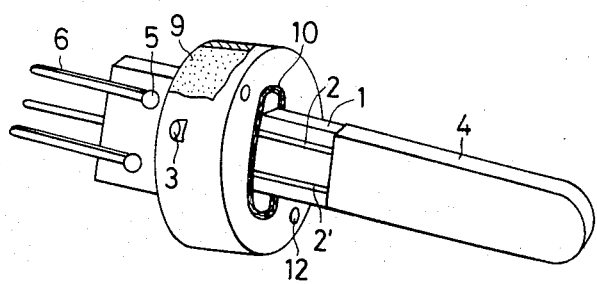
FIG. 4 is a perspective view of the gas sensor according to a third embodiment.

Referring to FIGS. 2 through 4 in which are shown typical embodiments of this invention, platinum paste is printed onto an alumina ceramic substrate 1 and then is sintered at a temperature above 1000° C., preferably in the range of between 1300° to 1400° C., so as to form platinum electrodes 2 and 2'. A powder (of 200 to 2000Å) of a p-type perovskite compound oxide is plasma-sprayed onto the substrate to form a p-type perovskite layer 3 straddling the two electrodes. By preheating the substrate to above 600° C., preferably to within the range of 700° C. to 1400° C., prior to the process of plasma spray coating, it is possible to obtain a spray coating layer with a strong adhesive force.

The thickness of the spray coating layer is several μm, and observations with a microscope shows that there are an extremely large number of fine cracks in the layer.

Then alumina powder with a particle size of less than several μm is plasma-sprayed to form a permeable inorganic insulative film 4 over the p-type perovskite layer. There are also large number of fine cracks in the insulative film 4.

Thereafter, the thus obtained composite bombardment film is immersed in a saturated solution of $NH_4VO_3$, and then the dried composite film is heated at temperature of between 1000° C. to 1400° C. for a period of several minutes to several hours, so that the $NH_4VO_3$ is decomposed and becomes an oxide which is diffused into the bombardment layer. This provides the target sensitive material layer.

Figure 2B:
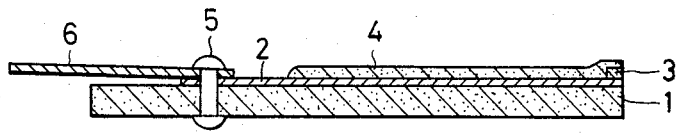
FIG. 2(b) is a side sectional view of FIG. 2(a)

Referring now to FIG. 2(b), which is a side view of FIG. 2(a), a lead terminal 6 made of stainless steel is fastened to a grommet 5 by silver soldering, after the vanadium compound into the perovskite layer 3 on the insulating substrate has been diffused as mentioned above. After the vanadium diffusion step, an insulating ceramic coating 4 is formed by, such as a spray coating method, on the platinum electrodes 2, 2' and the perovskite layer 3.

FIGS. 3(a) and 3(b) show another embodiment of this invention, in which a p-type perovskite layer is formed on one side of the alumina substrate used in the above sensor element, a resistance film 7 serving as a platinum heater and an electrode 2" thereof are formed on the other side of the substrate, and a permeable protective film 8 is formed by plasma spray coating of magnesia spinel.

When using the gas sensor of FIGS. 3(a) and 3(b), it is possible to obtain the desired sensitive characteristics even for low temperature gases present in, for example, an enclosed exhaust duct. That is, satisfactory sensitive characteristics can be achieved even in a low temperature atmosphere, by heating or preheating the sensor with the heater.

If a thermistor is provided instead of the heater, the sensor becomes able to both detect and control gas temperature.

FIG. 4 is a perspective view showing a typical mounting structure of the gas sensor according to this invention. When used in a field which requires a high heat resistance and mechanical strength, the sensor element shown in FIG. 2 and 3 is secured to a metal flange 11 via a mica plate 10 and heat resistant cement 9. The metal flange 11 is provided with mounting holes 12 and 13. The mounting structure and casing may be selected as required depending on the uses and purposes of the sensors, other than those of the embodiment shown in FIG. 4.

EXAMPLE 1

(a) Preparation of sensitive material powder

Powders of 1629 g $La_2O_3$, 747 g NiO and 2376 g $NaHCO_3$ were completely mixed with one another and then heated in an alumina crucible at a temperature of between 850° to 950° C. for about 10 hours under the atmospheric conditions. The heated powder was cooled and washed sufficiently with pure water. The resultant black-colored 1000 g of fine powder (of approximately 200 to 2000Å) of $LaNiO_3$ was added to 1 l of a saturated solution of $NH_4VO_3$, mixed, and then dried. The fine dried powder was heated at a temperature of about 900° C. for several minutes, and then heated at a temperature of 1350° C. for several hours. Thereafter, the thus heated powder was pulverized to obtain a p-type sensitive material powder with a particle size of several hundreds Å to several thousands Å.

(b) Manufacture of sensor

Platinum paste was screen-printed onto an alumina ceramic substrate (with a thickness of 0.6 mm) in the form of electrodes. After drying, the printed paste was sintered at a temperature of about 1350° C. in air. Then the p-type sensitive material powder prepared in the above process (a) was plasma-sprayed onto the substrate preheated to 800° C. to form a sensitive material layer with a thickness of 4 μm.

An alumina powder with an average particle size of 0.5 μm was plasma-sprayed onto the sensitive material layer to form a permeable inorganic insulative film with a thickness of 5 μm. Terminals were then fastened to the platinum electrodes by silver soldering to obtain the gas sensor shown in FIG. 2.

EXAMPLE 2

Platinum electrodes were formed on an alumina ceramic substrate by a method similar to that for process (b) in Example 1, and the p-type perovskite powder (not including diffused vanadium) obtained by process (a) in Example 1 was plasma-sprayed between the two electrodes to form a layer of sensitive material with a thickness of 3 μm. A permeable alumina insulative film with a thickness of 5 μm was then formed thereon in the same way as in process (b) in Example 1. The thus formed composite film was immersed in a saturated solution of $NH_4VO_3$ to seven times, so that $NH_4VO_3$ was impregnated into both the alumina insulative film and the sensitive material layer. After each impregnation, the sensor element was dried at temperature of between 20° to 100° C., was heated to under 500° to 950° C. to decompose the $NH_4VO_3$, and was then further heated to between 1250° to 1380° C. to promote the diffusion. Thereafter, the lead terminals were attached by soldering in the same way as in Example 1 to obtain a gas sensor.

EXAMPLE 3

By a method similar to that of process (b) in Example 1, platinum electrodes were formed on one side of an alumina ceramic substrate while a platinum resistance film was formed on the other side thereof. The p-type perovskite powder (not including diffused vanadium) obtained by process (a) in Example 1 was plasma-sprayed onto the side with the platinum electrodes, and then permeable inorganic insulative films were formed on both sides in the same way as in process (b) in Example 1 using fine alumina powder.

$NH_4VO_3$ was impregnated, decomposed and diffused by a method similar to that of Example 2, and lead terminals were attached in the same way as in Example 1. Then, after winding a mica plate round the connection portion, the sensor element was inserted into a flange made of stainless steel and was secured with a heat-resistant cement to obtain the gas sensor shown in FIG. 4.

EXAMPLE 4

By a method similar to that of Example 1 platinum electrodes were formed on both sides of an alumina ceramic substrate, and then a thermistor paste for high temperatures (the composition of the thermistor being the same as that disclosed in Japanese Patent Publication No. 3202/1982) was printed and sintered onto one side thereof. The p-type perovskite powder (including impregnated vanadium oxide) obtained by Example 1 was plasma-sprayed onto the other side, and then alumina insulative films were formed on both sides in the same way as in Example 1.

Thereafter, lead terminals were attached similarly to those in Example 1 and the thus obtained sensor element was secured to a flange made of stainless steel with a heat-resistant cement similarly to Example 3.

Various characteristics of the gas sensors thus obtained were measured. The results of these measurements will be explained hereinafter with reference to the drawings.

(a) Reduction of tailing effect

The gas sensor obtained by Example 2 was studied to determined how the reduction of the tailing effect was affected by the number of repeated impregnation and diffusion processes of the $NH_4VO_3$ solution.

Figure 5:
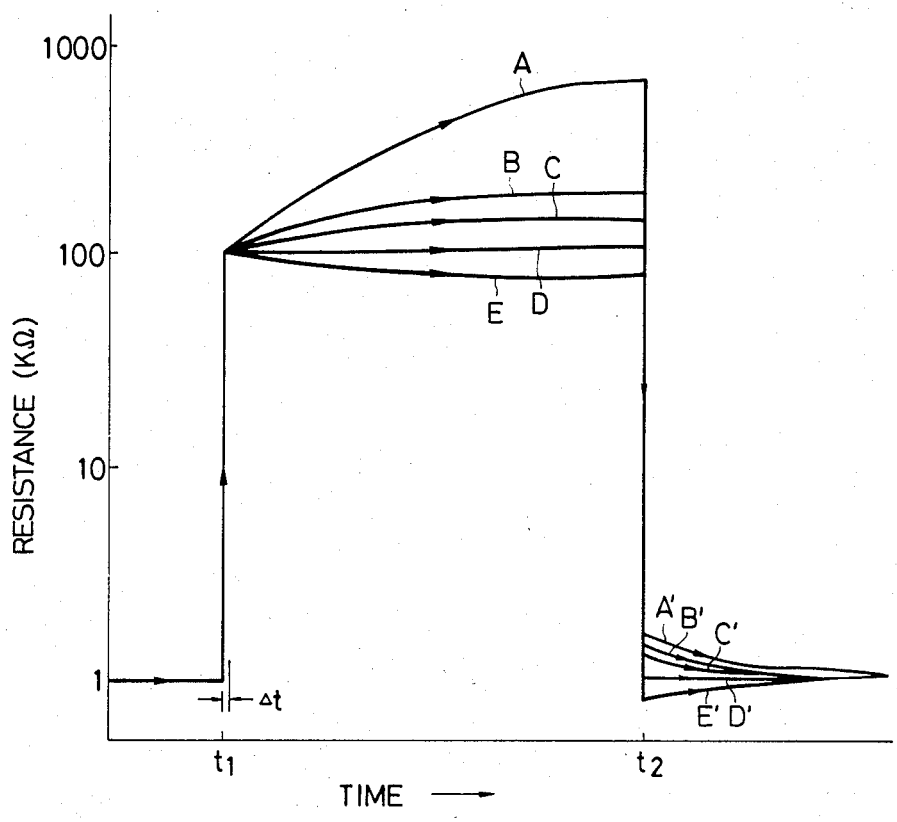
FIG. 5 is a graph showing the characteristics of the gas sensor according to one embodiment of this invention and a prior well-known gas sensor.

FIG. 5 shows the changes in the value of resistance of the gas sensor in a combustion flame of a mixture of 0.4 l/min of propane and 10 l/min or 7 l/min of air, which flame was produced using a burner including secondary air.

In FIG. 5, the period up to $t_1$ shows the resistance of the sensor when it was in the flame of a mixture of 0.4 l/min of propane and 10 l/min of air (i.e., in the perfect combustion region). The period from $t_1$ to $t_2$ (30 minutes) shows the resistance of the sensor in the flame when the flow rate of the air was reduced to 7 l/min with the propane remaining at 0.4 l/min, while the period subsequent to $t_2$ shows the resistance of the sensor in the flame when the flow rate of air was returned to 10 l/min.

The lines A and A' in the figure show a gas sensor in which $LaNiO_3$ was formed by plasma spray coating and which is similar to the one obtained in Example 2 except that the vanadium compound was not diffused.

B and B' represent a sensor of Example 2 which had the solution of $NH_4VO_3$ impregnated and diffused thereinto once, C and C' represent a sensor with the solution of $NH_4VO_3$ impregnated and diffused thereinto three times, D and D' represent a sensor with the impregnation and diffusion process repeated five times, and E and E' represent a sensor with the process repeated seven times.

These sensors showed identical characteristics, i.e., a resistance of 1 KΩ in the perfect combustion region (up to $t_1$). When the flow rate of air was changed to 7 l/min, the resistance increased to about 101 KΩ within a few milliseconds (Δt). This example indicates that a perovskite film formed by plasma spray coating has very high response.

However, when the sensors were in the imperfect combustion region ($t_1$ to $t_2$), even with no change in combustion conditions the resistance increased or decreased depending on the presence or absence of the diffused vanadium compound and the number of times the diffusion process was repeated, in some cases no change occurred in the value of the resistance.

As for the sensor which had no added vanadium compound, its resistance increased greatly (as indicated by the line A) in the period from $t_1$ to $t_2$.

The resistance of the sensor which had the vanadium compound impregnated and diffused thereinto once increased to about 110 KΩ (as indicated by the line B) in the period from $t_1$ to $t_2$, while the resistance of the sensor subjected to the impregnation and diffusion process three times increased to about 105 KΩ (line C). However, the resistance of the sensor subjected to the impregnation and diffusion process five times did not change and stayed at about 101 kΩ (the straight line D).

On the other hand, the resistance of the sensor subjected to the impregnation and diffusion process seven times decreased to about 80 KΩ (as indicated by the line E).

When the flow rate of air was returned to 10 l/m once again at time $t_2$, the resistance of the sensor with no diffused vanadium compound decreased (line A'), and similarly the resistances of other sensors decreased as indicated by the lines B' and C' in accordance with the number of times the diffusion process of the vanadium compound was repeated. The resistance of the sensor subjected to the diffusion process five times returned immediately to its original value of 1 KΩ and no change occurred thereafter (the straight line D'). The resistance of the sensor subjected to the impregnation and diffusion process more times first decreased to 0.9 KΩ and then gradually returned to 1 KΩ.

From the above, it will be apparent that diffusion of the vanadium compound can make it possible to reduce or eliminate the tailing effect when compared with a prior art sensor without the diffusion of such a compound.

(b) Durability

Various endurance tests were conducted on the gas sensors obtained in Example 2 through 4. The results of these tests are shown in FIGS. 6(a) through (c).

EXPERIMENT 1 (RESISTANCE TO FLAME TEST)

The resistance gas sensors initially, after 40 hours, 80 hours and after 500 hours were measured in a flame of 900° to 1100° C. with the flow rate of propane held at 0.4 l/min and the flow rate of air changed within the range of 6 to 11 l/min.

Figure 6A:
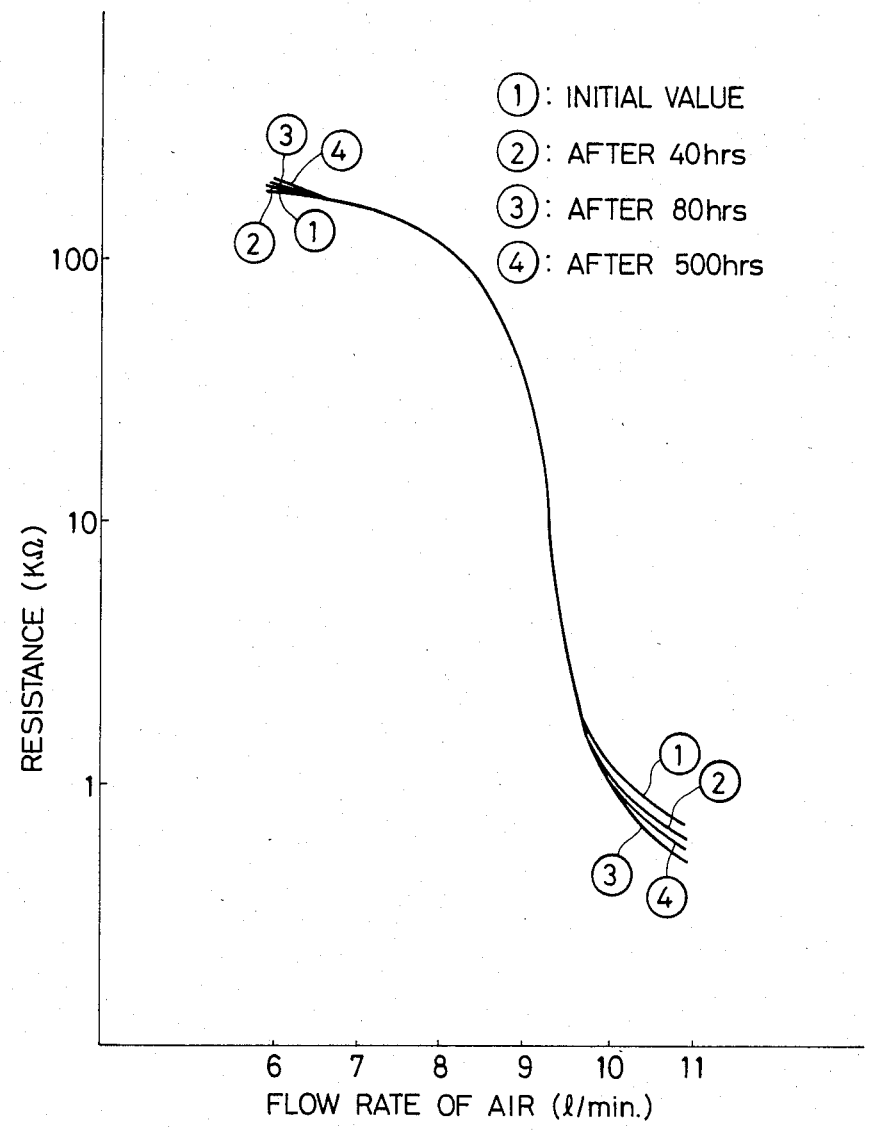
Figure 6C:
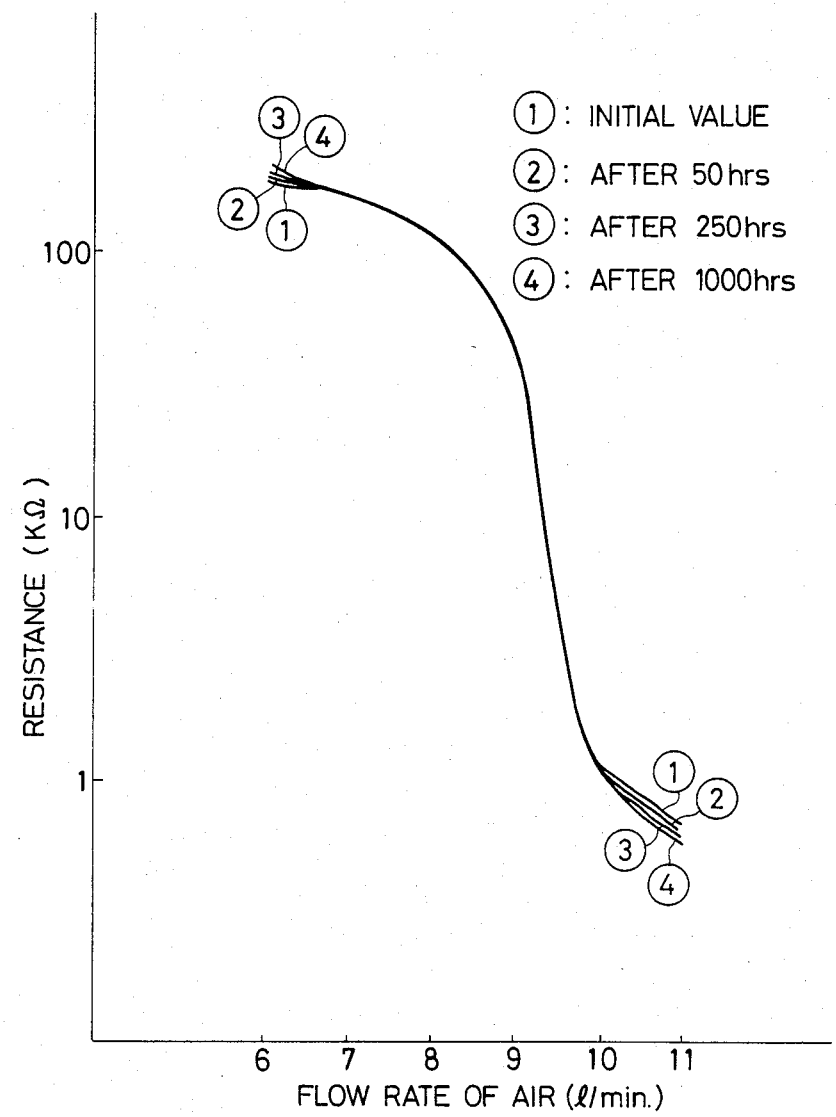

As can be seen from FIG. 6(a), the changes with time in the resistance of the gas sensor of this invention are very small.

EXPERIMENT 2 (HEAT RESISTANCE CYCLE TEST)

A heat resistance cycle test was conducted between 380° C. and 1050° C. (one cycle taking about 5 min.). The combustion conditions were the same as those of Experiment 1. The resistance was measured initially, after 1250 cycles, 2500 cycles and after 5000 cycles. It is apparent from FIG. 6(b) that the change in resistance was very small even after 5000 cycles.

EXPERIMENT 3 (HEAT RSISTANCE TEST)

Sensors were heated in air of 1000° to 1030° C. and their resistances were measured. As can be seen from FIG. 6(c), the changes in resistance were very small even after 10000 hours.

In both Experiments 1 and 2, the surface of the sensors became black with the carbon adhering thereto in the imperfect combustion region. But the tailing effect which results from such an adhesion of carbon was not apparent.

EXPERIMENT 4

Figure 7:
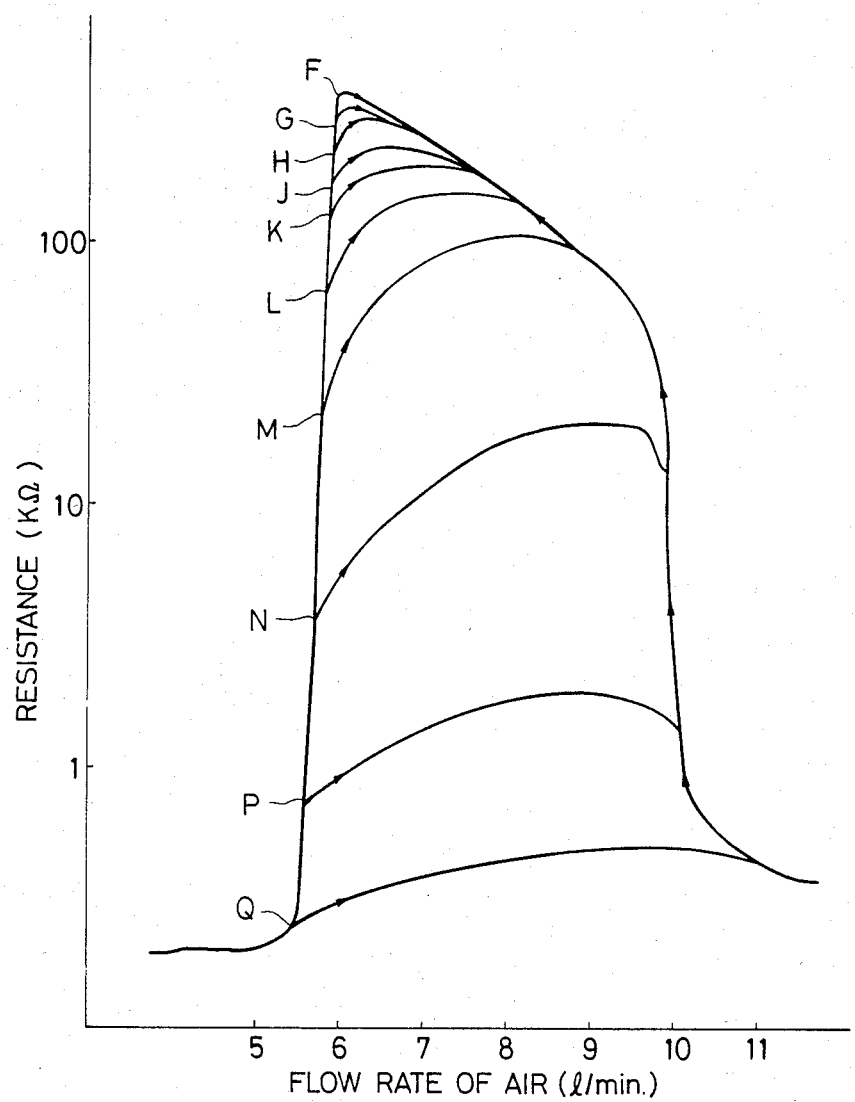
FIG. 7 is a graph showing the characteristics of the gas sensor according to one embodiment of this invention.

Changes in the resistance of the sensors obtained by Example 1 were measured with the flow rate of air reduced to less than 6 l/min with that of propane at 0.4 l/min. FIG. 7 shows the measured results.

Although the volumetric ratio of air/propane is never less than 15 in normal combustion, both the above artificial combustion and normal combustion were performed. As can be seen from FIG. 7, it was found that the resistance changed in different ways depending on the air/fuel ratios at which combustion conditions were returned from an excess carbon adhesion state to the normal state.

More specifically, a sensor was first set in a combustion flame with a flow rate of air of 5 (l/min), and then the flow rate of air was increased gradually. When the conditions were returned to normal combustion from a flow rate of air of 5.4, the resistance changed along a path indicated by the curve Q.

Likewise, the resistance changed along the curve P when returned from a flow rate of air of 5.6, the curve N from 5.7, the curve M from 5.75, the curve L from 5.8, the curve K from 5.85, the curve J from 5.86, the curve H from 5.87, the curve G from 5.88, and the curve F from 6. With these characteristics, the gas sensor of this invention is capable of detecting accurately the combustion state even when the air is too lean.

EXAMPLE 5

Figure 8A:
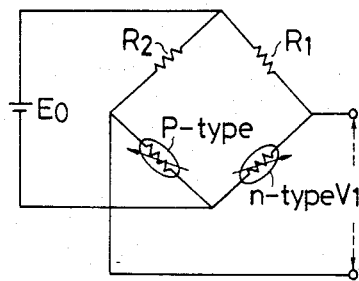
FIG. 8(a) is an equivalent circuit diagram of a composite gas sensor according to still another embodiment.
Figure 8B:
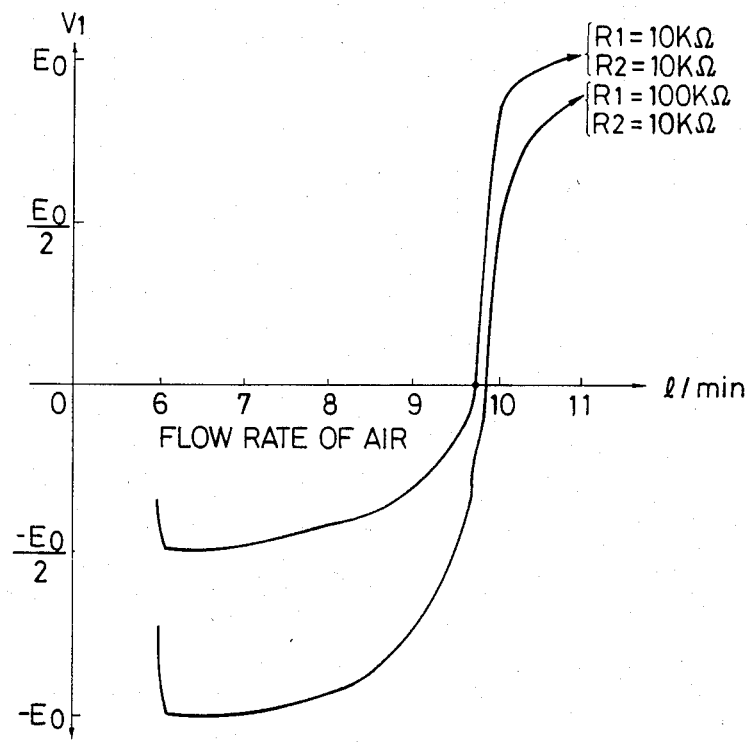
FIG. 8(b) is a graph showing the characteristics of the gas sensor of FIG. 8(a).

A $SnO_2$ film was formed instead of the high temperature thermistor film in Example 4. FIG. 8(a) shows the equivalent circuit diagram of the thus obtained sensor. Electromotive forces generated by the circuit in a flame were measured with $R_1$ and $R_2$ in FIG. 8(a) set at 10 KΩ and $R_1$ at 100 KΩ. FIG. 8(b) shows the measured results. In the measurements, the sensor was disposed with respect to a flame so that its electrodes were parallel to the incoming direction (i.e., the direction toward the center of the flame) of the secondary air.

As can be seen from FIG. 8(b), it is possible to obtain a sensor with a large electromotive force by combining p-type sensitive materials and n-type materials, due to the combined effects of both materials. This enables measurements or detection that include less errors caused by noise in the circuit.

EXAMPLE 6

A powder of a sensitive material of $LaNiO_3$ was prepared in the same as in Example 1. $NbCl_5$ and $Ta_6Cl_{14}$ were each added individually to and mixed with the sensitive material in a range of between 0.5 to 3%. After heat treatment at a temperature above the decomposition temperature of the additives, a diffusion process was carried out at 1000° C. for 50 hours. The thus obtained powder was plasma-sprayed onto an alumina substrate provided with platinum conductors in a similar way to that of Example 1. The thickness of the film was selected to be between 5 to 10 μm. Thereafter, the sensitive element thus obtained was tested in a propane combustion flame. As a result, it was discovered that the occurrence of the tailing effect could be largely prevented.

EFFECTS OF THE INVENTION

According to the invention, a gas sensor using a sensitive material can be obtained which has a small change with time and a reduced tailing effect attendant on variations in the gas composition being measured, e.g., changes in the combustion state. With this, it becomes possible to effect measurements, detection and control with a high reliability.

What is claimed is:

1. In a gas sensor comprising a layer of a sensitive material formed on an electric insulative substrate and electrodes electrically connected to said layer of sensitive material, the improvement wherein said layer of sensitive material is formed of a porous film consisting of a uniform mixture which contains a p-type compound oxide semiconductor with a perovskite type of crystal structure as the major ingredient and one or more materials selected from the group consisting of vanadium, niobium, tantalum and compounds thereof as minor ingredients, and wherein said layer of sensitive material has a thickness of 0.5 to 50 microns; said one or more materials selected from the group consisting of vanadium, niobium, tantalum and compounds thereof is contained in an amount of 0.01 to 5% by weight, based on the weight of the p-type compound semiconductor and is incorporated in the layer by diffusing said one or more materials selected from the group consisting of vanadium, niobium, tantalum and compounds thereof into the layer of said p-type compound oxide semiconductor; and said electrodes are electrically connected to said layer in remote relation to each other.

2. A gas sensor according to claim 1 wherein said layer of sensitive material is formed of a plasma spray coating film.

3. A gas sensor according to claim 1 wherein said layer of sensitive material is so formed that at least part of said minor ingredients is diffused into a plasma spray coating film consisting of said compound oxide semiconductor.

4. A gas sensor according to claim 1 wherein said layer of sensitive material is covered with a permeable inorganic insulative film.

5. A gas sensor according to claim 1 wherein said layer of sensitive material and said electrodes thereof as well as a heater having a resistance film and electrodes therefor are formed on said substrate.

6. A gas sensor according to claim 1 wherein a thermistor film and electrodes therefor as well as said layer of sensitive material and said electrodes therefor are formed on said substrate.

7. A gas sensor according to claim 1 wherein the semiconductor is a member selected from the group consisting of $LaNiO_3$, $LaCrO_3$, $LaTiO_3$, $LaCuO_3$, $PrTiO_3$, $CeTiO_3$, $La_{1-x}Sr_xVO_3$ ($0.1 \leq x \leq 0.4$), and $La_{1-x}Sr_xTiO_3$ ($0.1 \leq x \leq 0.4$).

8. A gas sensor according to claim 1 wherein the mixture consists essentially of said p-type compound oxide semiconductor and the one or more materials selected from the group consisting of vanadium, niobium, tantalum and compounds thereof.

9. A gas sensor according to claim 1 wherein the material of the electrodes is platinum.

10. A gas sensor comprising layer of a sensitive material formed on one flat surface of an electric insulative substrate and thin platinum electrodes deposited on and in contact with part of the surface of the layer in remote relation with respect to each other, wherein said layer is a porous spray coating of a thickness of 0.5 to 50 microns, said coating consisting essentially of a mixture of an oxide semiconductor of p-type perovskite crystal structure selected from the group consisting of $LaNiO_3$, $LaCrO_3$, $LaTiO_3$, $LaCuO_3$, $PrTiO_3$, $CeTiO_3$, $La_{1-x}Sr_xVO_3$ ($0.1 \leq x \leq 0.4$), and $La_{1-x}Sr_xTiO_3$ ($0.1 \leq x \leq 0.4$) and containing 0.01 to 5% by weight, based on the weight of the oxide semiconductor, of an additive selected from the group consisting of vanadium, niobium, tantalum, compounds thereof and combination thereof, where the additive is diffused by heating into the layer of the semiconductor.

11. A gas sensor according to claim 10 wherein said layer is covered with a gas permeable spray coating of ceramics.

12. A gas sensor according to claim 10 wherein a thermistor film and electrode films therefor are formed on the flat surface of another surface of the substrate.

13. A gas sensor according to claim 1 wherein said porous film consists of a uniform mixture which further contains n-type compound oxide semiconductor.

14. A gas sensor according to claim 1 wherein said electrodes are each formed on said substrate and spaced apart from each other relative to the surface of the substrate such that the electrodes are in remote relation to each other.

15. A gas sensor according to claim 1 wherein said p-type compound oxide semiconductor has a formula $ABO_3$, wherein A is a lanthanoid, part of which may be replaced by an alkaline earth metal, and B is a transition metal element.

16. A gas sensor according to claim 15, wherein said lanthanoid is selected from the group consisting of lanthanum, cerium and paseodymium, and said transition metal element is selected from the group consisting of nickel, chromium, titanium, copper, cobalt and vanadium.

* * * * *